US011027028B2

(12) United States Patent
Lascola (10) Patent No.: US 11,027,028 B2
(45) Date of Patent: *Jun. 8, 2021

(54) MANGANESE COMPLEXES WITH SUBSTITUTED BISPHOSPHONATES USEFUL AS IMAGING AND THERAPEUTIC AGENTS

(71) Applicant: DUKE UNIVERSITY, Durham, NC (US)

(72) Inventor: Christopher David Lascola, Durham, NC (US)

(73) Assignee: Duke University, Durham, NC (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/095,076

(22) PCT Filed: Oct. 26, 2016

(86) PCT No.: PCT/US2016/058845
§ 371 (c)(1),
(2) Date: Oct. 19, 2018

(87) PCT Pub. No.: WO2017/184200
PCT Pub. Date: Oct. 26, 2017

(65) Prior Publication Data
US 2019/0111160 A1    Apr. 18, 2019

Related U.S. Application Data

(63) Continuation-in-part of application No. PCT/US2016/028946, filed on Apr. 22, 2016.

(60) Provisional application No. 62/152,417, filed on Apr. 24, 2015.

(51) Int. Cl.
| | | |
|---|---|---|
| A61B 5/055 | (2006.01) | |
| A61K 49/10 | (2006.01) | |
| A61K 49/08 | (2006.01) | |
| A61K 47/54 | (2017.01) | |
| A61P 35/00 | (2006.01) | |
| A61K 9/00 | (2006.01) | |
| A61K 31/663 | (2006.01) | |
| A61K 31/675 | (2006.01) | |
| A61K 49/06 | (2006.01) | |

(52) U.S. Cl.
CPC .......... *A61K 49/103* (2013.01); *A61K 9/0019* (2013.01); *A61K 31/663* (2013.01); *A61K 31/675* (2013.01); *A61K 47/548* (2017.08); *A61K 49/085* (2013.01); *A61K 49/101* (2013.01); *A61P 35/00* (2018.01); *A61K 49/06* (2013.01); *A61K 49/106* (2013.01)

(58) Field of Classification Search
None
See application file for complete search history.

(56) References Cited

U.S. PATENT DOCUMENTS

| | | |
|---|---|---|
| 5,174,987 A | 12/1992 | Takaichi et al. |
| 8,247,572 B2 | 8/2012 | Kraus et al. |
| 2010/0247607 A1 | 9/2010 | Ashton |
| 2011/0021629 A1 | 1/2011 | Nelson et al. |
| 2012/0076770 A1* | 3/2012 | Espina ................ A61K 31/506 424/130.1 |
| 2014/0073780 A1 | 3/2014 | Bhushan et al. |
| 2014/0234210 A1 | 8/2014 | Lin et al. |
| 2014/0350193 A1 | 11/2014 | Axelsson et al. |
| 2015/0191471 A1 | 7/2015 | Haystead et al. |
| 2017/0189562 A1 | 7/2017 | Lascola |

FOREIGN PATENT DOCUMENTS

| | | |
|---|---|---|
| CN | 103930136 A | 7/2014 |
| JP | 2014520849 A | 8/2014 |

OTHER PUBLICATIONS

Song et al. (J. Chem. Soc. Dalton Trans. 2002, 2752-2759).*
Alanne, A-L. (2014) Novel Applications Related to Bisphosphorus Compounds [dissertations in Health Science]. Kuopio Finland: University of Eastern Finland, Faculty of Health Sciences. Publications of the University of Eastern Finland. Dissertations in Health Sciences No. 212. 2014. 68 p.*
Chinese Office Action corresponding to Patent Application No. 201680002995.2, dated Jul. 3, 2019 (17 pages including English translation).
Caravan et al. "Influence of molecular parameters and increasing magnetic field strength on relexivity of gadolinium- and manganese-based T1 contrast agents" Contrast Media Molecular Imaging: 4(2):89-100 (2009).
Crisponi et al. "Potentiometric and spectrophotometric equilibrium study on Fe(III) and near catechol-bisphosphonate conjugates" Journal of Inorganic Biochemistry, 102:209-215 (2008)
Demoro et al. "Bisphosphonate metal complexes as selective inhibitors of Trypanosoma cruzi farnesyl diphosphate synthase" Dalton Trans., 41:6468-6478 (2012).
El-Mabhouh et al. "A 99mTc-labeled gemcitabine bisphosphonate drug conjugate as a probe to assess the potential for targeted chemotherapy of metastatic bone cancer" Nuclear Medicine and Biology 33:715-722 (2006).
European Patent Office Examination Report, EP 16721317.2, dated Sep. 22, 2017.

(Continued)

*Primary Examiner* — Michael G. Hartley
*Assistant Examiner* — Melissa J Perreira
(74) *Attorney, Agent, or Firm* — Myers Bigel, P.A (57) ABSTRACT

Provided herein is a compound useful as a magnetic resonance imaging (MRI) contrast agent and a therapeutic agent, said compound having a structure represented by: Y—X—Z wherein, X is Mn(II), and Y and Z are each independently a bisphosphonate coupled to one or more therapeutic agents. Methods of use of the compound for MRI imaging and treatment for cancer or a microbial infection are also provided.

25 Claims, 5 Drawing Sheets

(56) References Cited

OTHER PUBLICATIONS

Hosain et al. "Targeted delivery of antineoplastic agent to bone: biodistribution studies of technetium-99m-labeled gem-bisphosphonate conjugate of methotrexate" J Nucl Med., 37:105-107 (1996).
International Search Report and Written Opinion, PCT/US2016/028946, dated Jul. 1, 2017.
International Search Report and Written Opinion, PCT/US2016/058845. dated Jan. 13, 2017.
Kushikbaeva et al.: "Solid Manganese(II) Hydroxyethylidenediphosphonates" Inorganic Chemistry, 2455-2460 (1988).
Lascola et al. "Drivable high spin Fe(III) and Mn(II) phosphonate scaffolds for MRI. International Society for Magnetic Resonance in Medicine" ISMRM, 2030 Addison Street, 7th Floor, Berkeley, CA 94701 USA. No. 2846, (2014) (Abstract only).
Lascola et al. "Drivable high spin Fe(III) and Mn(II) phosphonate scaffolds for MRI. Joint Annual Meeting of International Society for Magnetic Resonance in Medicine" ESMRMB, Milan, Italy. May 12-15, (2014) Poster.
Noebauer-Huhmann et al. "Gadolinium Magnetic Resonance Contrast Agents at 7 Tesla" Investigative Radiology, 45(9):554-558 (2010).
Sergienko "Structural chemistry of 1-hydroxyethylidenediphosphonic acid complexes" Russian Journal of Coordination Chemistry, 27(10):681-710 (2001).
Sergienko et al. "Crystal structure of triethanolammonium bis(1-hydroxyethane-1,1-diphosphonato)diaquazincate pentahydrate, [OHCH2CH2)3NH][Zn(H2O)2(H2.5L)2] 5H2O" Crystallography Reports, 45(2):262-265 (2000).
Gumienna-Kontecka et al. "Bisphosphonate chelating agents: complexation of Fe(III) and Al(III) by 1-phenyl-1-hydroxymethylene bisphosphonate and its analogues" Inorganica Chimica Acta, 339(15): 111-118 (2002).
Chinese Office Action corresponding to CN 201680086886.3; dated Nov. 2, 2020 (19 pages, including English translation).
Japanese Office Action corresponding to JP 2018-555227; dated Oct. 13, 2020 (9 pages, including English translation).
Gumienna-Kontecka, Elzbieta , et al., "Bisphosphonate chelating agents: complexation of Fe(III) and Al(III) by 1-phenyl-1-hydroxymethylene bisphosphonate and its analogues", Inorganica Chimica Acta, 339, 2002, 111-118.
Australian Examination Report corresponding to AU 2016252864; dated Mar. 10, 2021 (4 pages).
Australian Examination Report corresponding to AU 2016403775; dated Mar. 17, 2021 (4 pages).

\* cited by examiner

MANGANESE COMPLEXES WITH SUBSTITUTED BISPHOSPHONATES USEFUL AS IMAGING AND THERAPEUTIC AGENTS

RELATED APPLICATIONS

This application is a 35 U.S.C. § 371 national phase entry of PC Application PCT/US2016/058845, filed Oct. 26, 2016, which is a continuation-in-part of PCT Application PCT/US2016/028946, filed Apr. 22, 2016, which claims the benefit of U.S. Provisional Patent Application Ser. No. 62/152,417, filed Apr. 24, 2015, the disclosure of each of which is hereby incorporated by reference in its entirety.

GOVERNMENT FUNDING

This invention was made in part with government support under grant number W81XWH-12-1-0447 awarded by the Department of Defense. The United States government has certain rights in the invention.

BACKGROUND

Although advances in medical imaging and molecular diagnostics have improved early cancer detection and treatment, mortality rates for many of the most common malignancies have improved only marginally. Most patients who die from cancer succumb to metastatic disease and its associated complications. Chemotherapies successful in earlier stages invariably lose effectiveness once cancer spreads. Highly selective drugs targeting oncogenic signaling nodes (e.g., receptor tyrosine kinases) eventually lose potency as cells de-differentiate and become more genetically heterogeneous. Cytotoxic therapies with broad efficacy across a range of genetic profiles (e.g., anti-mitotic agents, radiation) are more capable of sustaining tumoricidal activity but are dose-limited by their off-target toxicity. There is a major need, therefore, for selective cancer therapies that maintain efficacy while minimizing toxicity.

The need for new therapies with low toxicity but sustained potency against mutable targets is now also critical for infectious disease. In less than a century, the number of microorganisms (e.g., bacteria, viruses, parasites, or fungi) resistant to approved drugs has risen exponentially. Antimicrobial resistance arises from the selective pressures driven by the drugs themselves, which are designed to target precise cellular pathways in microbial targets. Broadly active but less precise agents that are not susceptible to microbial resistance (e.g., alcohol, chlorhexidine, ultraviolet light) invariably possess unavoidable off-target toxicity. A fundamental challenge in both infectious diseases and cancer is, therefore, the same, and is to discover new therapies that may be resistant to target mutability while limiting off-target toxicity.

SUMMARY

One strategy for approaching the ideal of sustainable potency with minimal toxicity is to co-opt disease-avid molecules and introduce functional modifications that allow for image guidance in the delivery of cytotoxic (tumoricidal, microbidical) agents.

Therapies detectable in vivo using high resolution magnetic resonance imaging (MRI) provide a means for informing drug development at the earliest stages, enabling non-invasive assessment of pharmacokinetics and biodistribution in whole animals. Dual functionality is even more valuable in human studies, where understanding biodistribution and target concentrations of new therapies remain major challenges. In clinical practice, potential gains with approved agents are analogous, since all therapeutics demonstrate a range of biodistributive and pharmacokinetic behaviors across patient populations. MRI thus may be used as a tool for real-time monitoring of therapeutic delivery, enabling a personalized and optimized approach to drug administration in individual patients.

Provided herein is a compound useful as a MRI contrast agent and a therapeutic agent, said compound having a structure represented by:

wherein,

X is Mn(II), and Y and Z are each independently a bisphosphonate of the formula:

wherein:

$R^1$ is —OH, $R^2$, $R^3$, $R^4$, $R^5$ and $R^6$ are each independently H, alkyl (e.g., lower alkyl), or -LR', wherein at least one of $R^2$, $R^3$, $R^4$, $R^5$ and $R^6$ is -LR', wherein each L is present or absent and when present is a linking group, and wherein each R' is independently a therapeutic agent (e.g., a cytotoxin), or a pharmaceutically acceptable hydrate and/or salt thereof.

In some embodiments, $R^2$ is -LR', and $R^3$, $R^4$, $R^5$ and $R^6$ are each independently H or alkyl (e.g., lower alkyl).

In some embodiments, the compound has a stoichiometry of 1:2 (Mn(II):bisphosphonate).

In some embodiments, L comprises a poly(alkylene oxide).

In some embodiments, the compound is octahedral.

In some embodiments, the compound is a monohydrate or a dihydrate.

In some embodiments, the compound is a salt comprising from 1 to 3 cations (e.g., sodium, meglumine, etc.).

In some embodiments, the compound comprises: at least one water molecule coordinated with said Mn(II); at least one alkali metal or alkaline earth metal; and at least one additional cation.

In some embodiments, the compound comprises at least one alkaline earth metal selected from calcium and magnesium.

In some embodiments, the compound comprises sodium.

Also provided is a composition comprising a compound useful as a MRI contrast agent and a therapeutic agent as taught herein in a pharmaceutically acceptable carrier. In some embodiments, the pharmaceutically acceptable carrier is water or phosphate buffered saline.

Further provided is a method of performing a MRI scan on a subject comprising administering the compound or composition as taught herein to said subject prior to and/or during the MRI scan.

Also provided is a method of administering a therapeutic agent to a subject in need thereof, comprising administering the compound or composition as taught herein to said subject in a treatment effective amount. In some embodiments, the method further includes detecting the MRI contrast agent in said subject with MRI. In some embodiments, the administering is adjusted (e.g., placement of needle(s), dosage, rate of delivery, etc.) based upon said detecting.

In some embodiments, the subject is in need of treatment for cancer.

In some embodiments, the subject is in need of treatment for a microbial infection (e.g., a recalcitrant or chronic bacterial infection).

Further provided is the use of a compound or composition as taught herein for carrying out a method of treatment as taught herein, or for the preparation of a medicament and/or imaging agent for carrying out a method as taught herein.

BRIEF DESCRIPTION OF THE DRAWINGS

FIG. 3. A, A 2:1 complex of 1-OH bisphosphonate and Mn$^{2+}$ is thermodynamically favored. By varying stoichiometry during synthesis, no additional complexation of Mn$^{2+}$ is observed when the ratio of bisphosphonate to Mn$^{2+}$ is raised above 2:1. Free Mn$^{2+}$ is determined by measuring solvent $T_2$ as a function of time, since $r_2$ of Mn$^{2+}$ is 30-fold that of fully chelated, monohydrated Mn$^{2+}$ (Caravan et al., Mol. Imaging 2009, 4:89). B, Alkali metal cations increase the stability of the 2:1 bisphosphonate:Mn$^{2+}$ complex. Heteronuclear complexes containing at least one Na$^+$ cation and at least one Ca$^{2+}$ cation form the most stable 2:1 complexes, resulting in complete chelation of mono-hydrated Mn$^{2+}$ without excess ligand. Horizontal dotted line indicates the point at which $r_2$ becomes 30-fold less than the value of MnCl$_2$ in solution. C, ESI MS of a heteronuclear 2:1 etidronate:Mn complex two months after synthesis, confirming its stability and stoichiometry. C$_4$H$_9$O$_{14}$P$_4$:Mn$^{2+}$:Ca$^{2+}$:Na$^+$ (m/z=522.8).

FIG. 6. PK and biodistribution of 2:1 etidronate:Mn$^{2+}$ complex synthesized with Na$^+$ and Ca$^{2+}$ (C$_4$H$_9$O$_{14}$P$_4$: Mn$^{2+}$:$_x$Ca$^{2+}$:$_x$Na$^+$). A, Dynamic contrast-enhanced (DCE) analysis of contrast agent over 60 mins following intravenous administration. Peak enhancement in organs and musculoskeletal system tracks in time with changes in aorta, indicating the contrast agent remains intact and extracellular. B, DCE analysis of excretory systems shows intact elimination through kidneys and liver/gallbladder. C, Normalized color lute T1 weighted images showed relative changes in organ systems over the first 60 mins, then at 24 and 48 hours. At 24 hours, no residual contrast changes are seen throughout the subject except in kidneys. The latter changes are nearly resolved by 48 hours. Higher signal intensity changes in the stomach at 24 and 48 hours (left upper quadrant) are secondary to incidental paramagnetism in the feed.

DETAILED DESCRIPTION

Described herein according to some embodiments is image-guided therapy that uses well-defined, stable manganese bisphosphonate complexes as a biocompatible strategy for paramagnetic labeling of therapeutic agents. Bisphosphonate ligands may be coupled to one or more therapeutically active agents using a variety of chemical approaches for covalent linkage, creating conjugate molecules that can be followed in vivo in real-time using clinical MRI. In some embodiments, MRI may be used to optimize dosing of these conjugates, whether they are administered through oral, intramuscular (IM), intravenous (IV), directed intravascular, intra-thecal, or percutaneous routes, enabling disease-specific delivery of broadly-effective, sustainable and minimally-toxic therapies under image guidance.

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

As noted above, provided herein are compounds useful as contrast agents and therapeutic agents. "Compound" as used herein refers to a molecule having atoms held together via covalent, coordinate and/or ionic bonds.

"Contrast agent" as used herein is a substance used to enhance the contrast of structures or fluids within the body in medical imaging. Examples of known contrast agents include, but are not limited to, radiocontrast agents and MRI contrast agents.

A "radiocontrast agent" is a substance that can enhance the contrast of structures or fluids within the body during an x-ray-based scan. Examples include, but are not limited to, iodine and barium.

An "MRI contrast agent" is a substance (e.g., compound and/or complex) that can enhance the contrast of structures or fluids within the body during an MRI scan. Examples include, but are not limited to, paramagnetic contrast agents such as gadolinium(III) containing agents or manganese chelates, and superparamagnetic agents such as iron platinum particles. See U.S. Patent Application Publication Nos. 2014/0350193 to Axelsson et al.; 2014/0234210 to Lin et al.

In some embodiments, the use of a contrast agent of the present invention may enhance "attenuation" or "signal" in diseased tissues of a subject where contrast material transiently accumulates in the extracellular compartment (interstitium) of diseased regions after the "first pass" through the blood vessels. Accordingly, tissue enhancement is often observed in tumors, infection, inflammation, demyelination, and acutely infarcted tissue.

In some embodiments, contrast agents as taught herein have a molecular weight of less than 2,000 daltons, 1,500 daltons, 1,000 daltons, 800 daltons, or 500 daltons. Such low molecular weight contrast agents may enhance the imaging of tissues by, e.g., allowing diffusion from blood through diseased "leaky" blood vessels.

In some embodiments, contrast agents comprise high spin manganese (Mn(II), having 5 unpaired electrons) complexed with bisphosphonates.

In some embodiments, the bisphosphonate is a substituted 1-hydroxybisphosphonate. In some embodiments, the 1-hydroxybisphosphonate is substituted with a therapeutic agent.

In some embodiments, the bisphosphonate has a formula:

wherein: $R^1$ is —OH; $R^2$, $R^3$, $R^4$, $R^5$ and $R^6$ are each independently H, alkyl (e.g., lower alkyl such as $C_1$ alkyl, $C_2$ alkyl, $C_3$ alkyl, or $C_4$ alkyl), or -LR', wherein L is present or absent and when present is a linking group, and R' is a therapeutic agent (e.g., a cytotoxin). In some embodiments, at least one of $R^2$, $R^3$, $R^4$, $R^5$ or $R^6$ is -LR'.

"Alkyl," as used herein, refers to a saturated straight or branched chain, or cyclic hydrocarbon containing from 1 to 10 carbon atoms (i.e., $C_{1-10}$). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclopropyl, cyclobutyl, cyclopentyl, cyclohexyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, cyclopropyl, cyclobutyl, and the like.

In some embodiments, where L is absent, the bisphosphonate is coupled directly to a therapeutic agent (such as a cytotoxin) prior to metal complexation. In some embodiments, the linking group L is present, and may include an alkylene, alkylenecarbonyl, carbonylalkylene, a carbonyl group, maleimide, alkylamino, poly(alkylene oxide) or polyether such as polypropylene glycol or polyethylene glycol (PEG), combinations thereof, etc. See also U.S. Pat. No. 4,179,337 to Davis et al.; U.S. Pat. No. 7,122,189 to Zhao et al.; U.S. Pat. No. 8,247,572 to Kraus et al.; US 2009/0285780 to Lee.

The linking group L in some embodiments is attached at the $R^2$ position. Linking group L in some embodiments is attached at the $R^3$, $R^4$, $R^5$ and/or $R^6$ position.

In some embodiments, L may be an alkylene, alkylenecarbonyl, carbonylalkylene, a carbonyl group, or maleimide as follows:

wherein n is 0 (i.e., a direct covalent linkage) or is from 1 to 6. Such alkylene groups may be saturated or unsaturated, and may be substituted 1, 2, 3, or 4 times with C1-C4 alkyl, halo, phenyl, or halo-substituted phenyl. Examples are as follows:

A phenyl or phenylene group, or two or more linked phenylene groups, may be provided as the linking group, which phenylene group may optionally be substituted 1, 2, 3 or four times with a halogen or alkyl group. Examples are as follows:

A substituted or unsubstituted phenylene group may be joined at either or both ends with a substituted or unsubstituted alkylene, alkylenecarbonyl, carbonylalkylene, or carbonyl group as described above to provide a linking group. Examples are as follows:

A substituted or unsubstituted alkylene, alkylenecarbonyl, carbonylalkylene, or carbonyl group as described above may be joined at either or both ends to a substituted or unsubstituted phenylene group as described above to provide a linking group. Examples are as follows:

-continued where "n" is as defined above. Such compounds may be further substituted at either or both ends by a substituted or unsubstituted alkylene, alkylenecarbonyl, carbonylalkylene, or carbonyl group, as described above, to provide still further linking groups. Examples are as follows:

where "n" is as defined above.

Linking groups as described above can be coupled one to the other (e.g., a maleimide group to an alkyl chain) to produce still other linking groups useful for carrying out the present invention.

Further examples of linking groups are described in U.S. Pat. Nos. 6,872,841; 6,607,741; 6,624,317; 6,593,334; 6,566,393, 6,420,377; and 6,207,673.

High spin Mn(II) is an excellent candidate paramagnetic metal possessing 5 unpaired electrons, favorable electronic relaxation and water residence times ($T_m \ll T_1$) for MRI enhancement. As a free metal, Mn is also less toxic than Gd, with a natural pool and several homeostatic mechanisms for processing.

In the past, development of paramagnetic Mn complexes for MRI has been challenged by the inherent coordination lability of Mn(II) (e.g., Irving Williams series), resulting in the propensity of Mn(II) to be trans-metallated by other endogenous metals such as zinc in vivo. However, the Mn(II) bisphosphonate complex disclosed herein has a remarkable in vivo stability, remaining intact when used either alone as a tissue contrast material or coupled to other small molecule drugs. When used alone, it is eventually eliminated either through the kidneys and liver/gallbladder/bowel on a time course similar to commercial Gd-based contrast materials.

In some embodiments, the Mn bisphosphonate compound has a stoichiometry of: 1 Mn:2 bisphosphonate (e.g., etidronate); has at least one coordinated $H_2O$ (e.g., monohydrate or dihydrate); has at least one alkali metal (e.g., Na+, K+) or alkaline earth metal (e.g., Ca++ or Mg++); and/or has at least one additional cation (e.g., Na+, meglumine, etc.). In some embodiments, the Mn bisphosphonate compound has a stoichiometry of: 1 Mn:2 bisphosphonate (e.g., etidronate):1 alkali metal (e.g., Na+, K+):1 alkaline earth metal (e.g., Ca++ or Mg++).

In some embodiments, the contrast agent has an $r_2$ relaxivity of 5, 8 or 10 to 15, 18, 20, 25, 30, 35 or 40 $mM^{-1}sec^{-1}$ measured at 7 Tesla (e.g., at 22 degrees Celsius, 2 mM Tris buffered $ddH_2O$, and/or pH 7.0). Without wishing to be bound by theory, free Mn in solution (e.g., $MnCl_2$ salt) has low $T_2$ relaxation/high $r_2$ relaxivity ($mM^{-1}sec^{-1}$) because of both increased T2* susceptibility as well as spin-spin (T2') effects. T2 (and, thus, r2) are a function of both T2* and T2'. Hydrated, free ions cluster together with several coordinating inner sphere waters, increasing local magnetic field inhomogeneity and spin-spin interactions between bound and solvent water molecules. When individual Mn ions are coordinated with a ligand, clustering and, therefore, T2* effects (and $r_2$ relaxivity) are reduced. Strong Mn complexes with only one coordinating inner sphere water also possess decreased spin-spin interactions, and, therefore, T2' effects by virtue of less exchange between bound and solvent water molecules. When individual Mn ions become fully complexed with a ligand chelate in solution, measured $r_2$ of the chelate metal has been previously determined to be 30 fold less than the free metal in solution. See Caravan et al., Mol. Imaging 2009, 4:89. Thus $r_2$ can be a marker of the degree of complexation. See also FIG. 3.

The complexation of the metal may lead to reduced toxicity and/or increased stability of the contrast agent. Free metal such as Mn administered intravenously can have immediate deleterious toxicity effects. For free Mn, in particular, cardio toxicity may be a concern because of negative chronotropic/ionotropic effects. PK/biodistribution differences are seen, e.g., with 1:1 Mn:bisphosphonate complex versus the 1:2 complex, as well as with synthesis with cations such as meglumine and choline instead Na+ and Ca++(data not shown). Toxicity may also have been detected during injections, with rapid cardio and respiratory suppression at equivalent doses that is not seen with Na+ and Ca++1:2 Mn:bisphosphonate complexes (data not shown).

As taught herein, a contrast agent may comprise one or more therapeutic agents. In these embodiments, real-time monitoring of the delivery of the therapeutic agent(s) may be performed by detection of the contrast agent, providing an accurate representation of where the therapeutic agent is delivered ("theranostics").

The term "pharmaceutically acceptable" as used herein means that the compound or composition is suitable for administration to a subject to achieve the treatments described herein, without unduly deleterious side effects in light of the severity of the disease and necessity of the treatment.

In some embodiments, the contrast agent is coupled to, e.g., covalently coupled to, a therapeutic agent such as a cytotoxin. "Cytotoxin" as used herein refers to an agent that causes cell death, such as an anti-cancer agent, an antimicrobial, or other cell death causing agents. Examples include, but are not limited to, interferon, methotrexate, doxorubicin, daunorubicin, vincristine, vinblastin, mitomycin C, bleomycin, taxol, taxotere, navelbine, adriamycin, amphipatic amines, chloroquine, hydroxychloroquine, and the like.

Example classes of cytotoxins include, but are not limited to: alkylating agents, such as nitrogen mustards, alkyl sulfonates, nitrosoureas, ethylenimines, and triazines; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as paclitaxel, docetaxel, combretastatins A, B, C and D and their derivatives, hydrates, and prodrugs (such as combretastatin A-4 phosphate), and epothilones A-F, as well as their analogs, prodrugs, hydrates, solvates, or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers (e.g., tyrosine kinase inhibitors such as lapatinib), growth factors; immune modulators, antimalarial drugs (e.g., chloroquine, hydroxychloroquine) and monoclonal antibodies. The compounds of the invention may also be used in conjunction with radiation therapy, as appropriate.

Further representative examples of classes of cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil (5-FU), 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Antimicrobials may include, but are not limited to, antibiotics. Example antibiotics include, but are not limited to, aminoglycosides such as amikacin, gentamicin, kanamycin, neomycin, netilmicin, tobramycin, paromomycin, streptomycin, spectinomycin; ansamycins such as geldanamycin, herbimycin, rifaximin; carbacephems such as loracarbef; carbapenems such as ertapenem, doripenem, imipenem, meropenem; cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole; glycopeptides such as teicoplanin, vancomycin, televancin, dalbavancin, oritavancin, clindamycin, lincomycin; lipopeptides such as daptomycin; macrolides such as azithromycin, clarithromycin, dirithromycin, erythromycin, roxithromycin, troleandomycin, telithromycin, spiramycin; monobactams such as aztreonam; nitrofurans such as furazolidone, microfurantoin; oxazolidinones such as linezolid, posizolid, radezolid, torezolid; penicillins such as amoxicillin, ampicillin, azolcillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin; polypeptides such as bacitracin, colistin, polymyxin B; quinolones such as ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin; sulfonamides such as mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine; tetracyclines such as demeclocycline, doxycycline, minocycline, oxytetracycline, tetracycline; agents useful in treatment for mycobacteria such as clofazimine, dapsone, capreomycin, cycloserine, ethambutol, ethionamide, isoniazid, pyrazinamide, rifampin, rifabutin, rifapentine, streptomycin; other antimicrobials such as arspenamine, chloramphenicol, fosfomycin, fusidic acid, metronidazole, mupirocin, platensimycin, quinupristin/dalfopristin, thiamphenicol, tigecycline, tinidazole, trimethoprim, teixobactin, etc., including combinations thereof.

In some embodiments, the cytotoxic agents may include, but are not limited to, tetracycline, methotrexate, lapatinib, aminoquinolines such as chloroquine and hydroxychloroquine, and HSP-90 inhibitors. See, e.g., U.S. Patent Publication No. 2006/0074105 to Ware, Jr., et al.; U.S. Patent Publication No. 2015/0191471 to Haystead et al.

Methods of Use

The present invention is primarily concerned with the scanning and/or treatment of human subjects, but the invention may also be carried out on animal subjects, particularly mammalian subjects such as mice, rats, dogs, cats, livestock and horses for veterinary purposes, and/or for drug screening and/or drug development purposes.

The term "treat" as used herein refers to any type of treatment that imparts a benefit to a subject afflicted with a disease, including improvement in the condition of the subject (e.g., in one or more symptoms), delay in the progression of the disease, etc.

The imaging and therapeutic agents as taught herein are detectable in vivo and provide the opportunity for a personalized MRI-guided therapy by enabling non-invasive assessment of pharmacokinetics and biodistribution of the coupled therapeutic agent on an individual basis. Even well-characterized, approved therapeutic agents can have a wide range of pharmacokinetic and biodistrubutive behaviors across patient populations; thus, real-time monitoring of agent delivery can maximize therapeutic efficacy and minimize toxicity for a particular subject.

The imaging and therapeutic agents as taught herein may also enable personalized MRI-guided local treatment of a tumor. Most chemotherapy drugs are delivered systemically; however, MRI-guided treatment may allow monitored local delivery, ensuring the therapeutic agent is accumulating at its intended target. Further, the delivery placement and/or dosing may be adjusted during treatment.

For example, delivery of an ablative cytotoxic agent as part of a contrast agent as taught herein can be guided and monitored in real-time by MRI, ensuring that the agent reaches its intended target (e.g., a tumor) and does not unduly distribute to other tissues causing unwanted toxicity.

In some embodiments, the treatment is performed before or after surgical resection of a tumor. In some embodiments, the treatment is for a "non-resectable" cancer (i.e., one for which surgical resection is not recommended by applicable medical guidelines) or "borderline resectable" cancer (e.g., locally advanced, non-metastatic pancreatic cancer). In such a case, ablative cytoxic agents complexed to a contrast agent as taught herein can be guided to the cancer, with adjustment to local delivery as needed, to treat the cancer. In some embodiments, treatment may result in the cancer subsequently being rendered resectable.

The imaging and therapeutic agents as taught herein may also enable personalized MRI-guided local ablative treatment of an infection. MRI-guided treatment may allow monitored local delivery, ensuring the therapeutic agent is accumulating at its intended target to reduce an infection, such as bacteria/bacterial biofilm, infected host tissue, etc. Further, the delivery placement and/or dosing may be adjusted during treatment.

For example, delivery of an antimicrobial agent as part of a contrast agent as taught herein can be guided and monitored in real-time by MRI, ensuring that the agent reaches its intended target (e.g., the site of a microbial infection such as a bacterial, viral, or fungal infection) and does not unduly distribute to other tissues causing unwanted toxicity and/or side effects.

In some embodiments, the infection is recalcitrant (i.e., resistant to one or more therapies) or chronic (i.e., lasting at least six months).

The present invention is explained in greater detail in the following non-limiting examples.

EXAMPLES

Example 1: Low Molecular Weight Manganese Bisphosphonate Complex for Molecular Imaging and Multiplexed Therapy Example Synthesis of High-Spin Mn(II) Complex To a desired final volume of double distilled water and under constant stirring, add 2 equivalents of etidronic acid and 4 equivalents of sodium bicarbonate. The pH of the solution will be approximately 3.8-4.0 after 10 minutes. The pH may then be adjusted further by dilute NaOH to approximately 5.5-7.0. Following this, 1 equivalent of $MnCl_2$ is added. After $MnCl_2$ addition, the solution will, as expected, become more acidic (pH approximately 3-4), but pH should be raised with moderately dilute base such as NaOH to 7.0-7.5. The most consistent and effective results have been achieved when the pH is between 5-7 before addition of Mn(II), and an alkali metal cation (e.g., Na) is present in advance to coordinate at least with the two phosphate oxygens on etidronate, which have pKa's of 0.70 and 1.46.

A mildly basic amine buffer such as Tris may be employed initially or after addition of primary reagents with good result to ensure a pH of neutrality or greater, although at least two Na+ equivalents per molecule of etidronic acid before addition of Mn seems particularly beneficial. Heat for this reaction is not necessary.

The product may be precipitated and isolated with excess polar organic solvent (e.g., acetone, MeOH, ETOH); however, this particular complex is more soluble (less hydrophilic) in these solvents and so precipitation and isolation requires more time and challenge. Alternative isolation of final solid product is also achievable by direct freeze-drying.

In vivo behavior was tested of two relatively strong (log $K_1$>7) ligands for Mn(II) chelation, nitrilotriacetic acid (NTA), closely related to EDTA, and 3,4-dihydrobenzoic acid (3,4-DBA). Both readily form Mn(II) coordination complexes and show relaxation profiles similar to commercial Gd chelates. In vivo MR imaging of these agents after i.v. administration, however, revealed identical biodistributions for both NTA and 3,4-DBA, consistent with release of free Mn and hepatocellular uptake, i.e., strong parenchymal enhancement, absence of gallbladder enhancement, and no evidence for renal elimination (FIG. 4A).

This in vivo behavior was also what was observed for the previously FDA-approved agent Teslascan (mangafodipir trisodium). In the past, development of paramagnetic Mn complexes for MRI has been challenged by the inherent coordination lability of Mn(II) (e.g., Irving Williams series), resulting in the propensity of Mn(II) to be trans-metallated by other endogenous metals such as zinc in vivo. The only FDA-approved approved Mn(II) PM complex for MRI was Teslascan, which has now been discontinued. Teslascan immediately distributed to the liver, releasing free Mn that was then taken up by hepatocytes. Contrast enhancement was, therefore, based on free Mn and confined to the liver. In addition, cardiac enhancement was also seen for both NTA and 3,4-DBA, indicating free Mn released into the blood pool before entering the liver.

Figure 4:
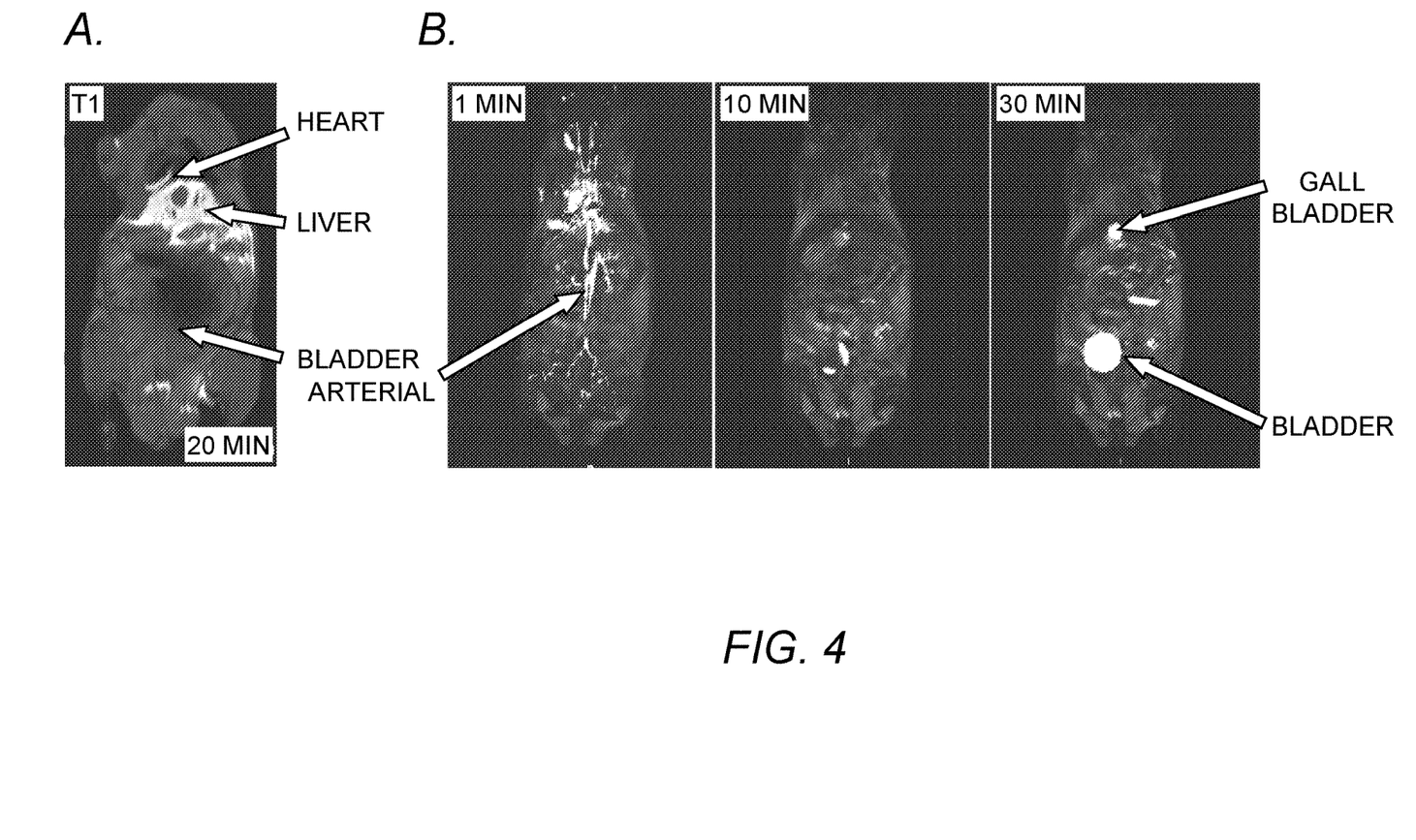
FIG. 4. A, In vivo MRI in control mouse after i.v. administration of MnNTA. B, MRI after i.v. administration of Mn:ETID (50 L of 40 mM solution).

In comparison to NTA and 3,4-DBA, IV administration of 30 mg/kg Mn(II)etidronate initially reveals a striking arterial blood pool phase, followed by rapid enhancement of the renal collecting system and urinary bladder as well as gallbladder (FIG. 4B). Enhancement of the liver parenchyma is observed, although substantially less intense than NTA and 3,4-DBA, peaking at 10-15 minutes after administration and returning to normal $T_1$ values by 4 hours. Enhancement of the bowel is also noted but more variable, believed to represent elimination of the coordination complex from the gallbladder into the small intestine. In addition, subtle but transient $T_1$ changes are observed in the skeletal muscles and long bones that return to normal after 30 min, paralleling the mild residual $T_1$ changes in major vessels, consistent with a blood pool rather than local parenchymal uptake effect. No $T_1$ changes are observed in brain or spine (n=20).

Example 2: Differences in Complexation of Mn in Contrast Agents

Figure 1:
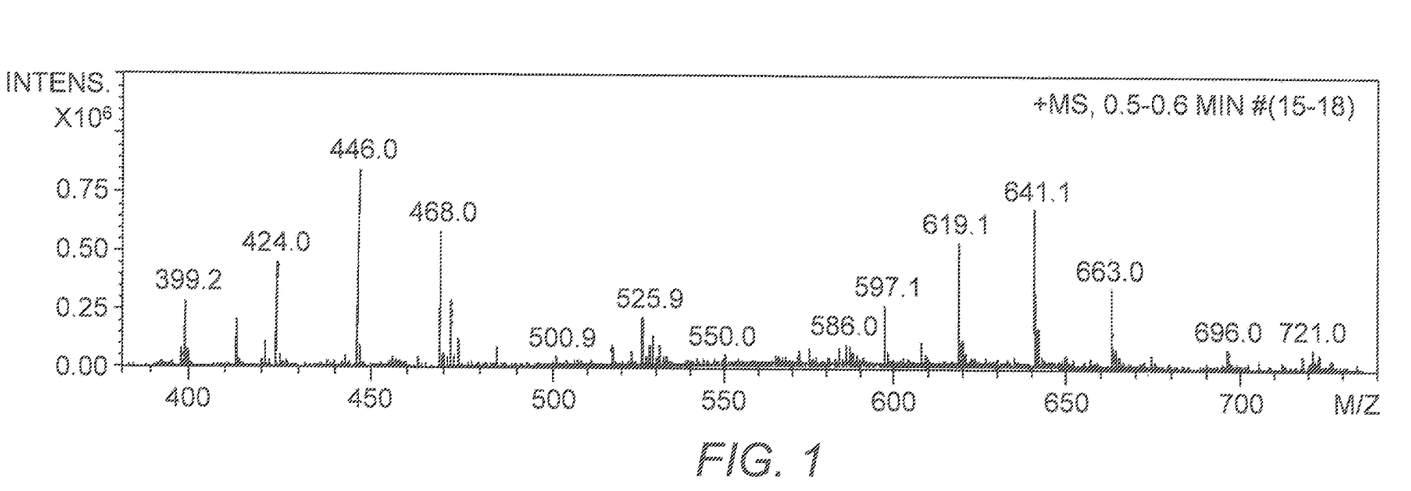
FIG. 1. Positive mode electrospray ionization mass spectrometry (ESI MS) of paramagnetic Na:Mn(Etidronate)$_2$ complex with additional Na or meglumine as salt adducts. Each represents the base peak of the designated complex after loss of the PO$_3$ fragment during ionization. 1Na: C$_4$H$_{11}$O$_{11}$P$_3$:Mn:H$_2$O (m/z=424). 2Na:C$_4$H$_{10}$O$_{11}$P$_3$:Mn: H$_2$O (m/z=446) 3Na:C$_4$H$_9$O$_{11}$P$_3$:Mn:H$_2$O (m/z=468) 1Na: C$_4$H$_{10}$O$_{11}$P$_3$:Mn:H$_2$O:C$_7$H$_{17}$NO$_5$ (m/z=619.1) 2Na: C$_4$H$_{10}$O$_{11}$P$_3$:Mn:H$_2$O:C$_7$H$_{17}$NO$_5$ (m/z=641.1) 3Na: C$_4$H$_9$O$_{11}$P$_3$:Mn:H$_2$O:C$_7$H$_{17}$NO$_5$ (m/z=663.0)
Figure 2:
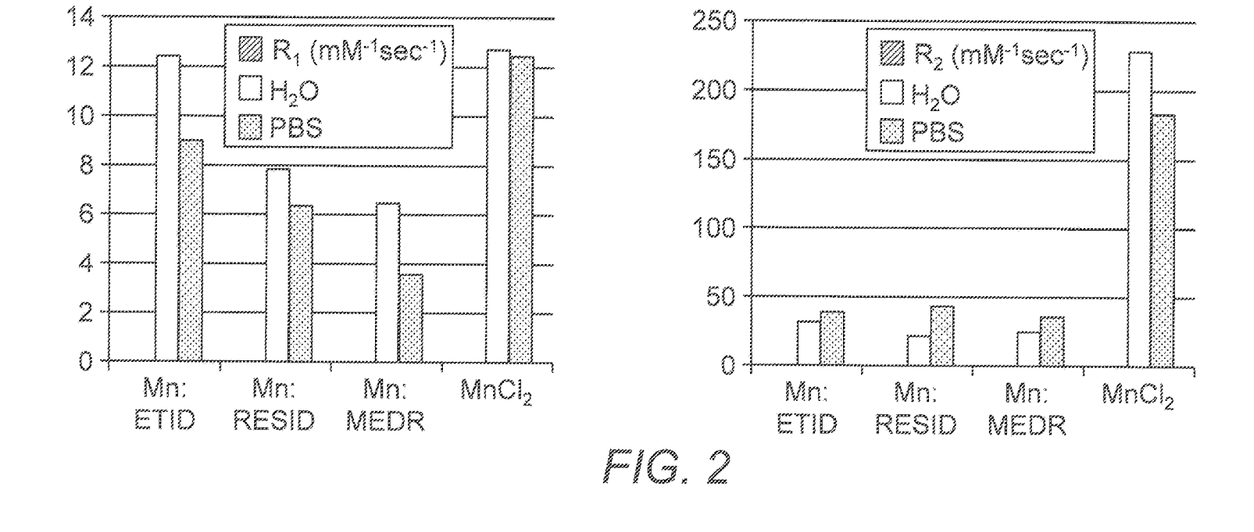
FIG. 2. $T_1$ and $T_2$ relaxivities ($r_1$, left and $r_2$, right) of Mn bisphosphonate complexes with commercially available bisphosphonates, as compared to free Mn(II).
Figure 3:
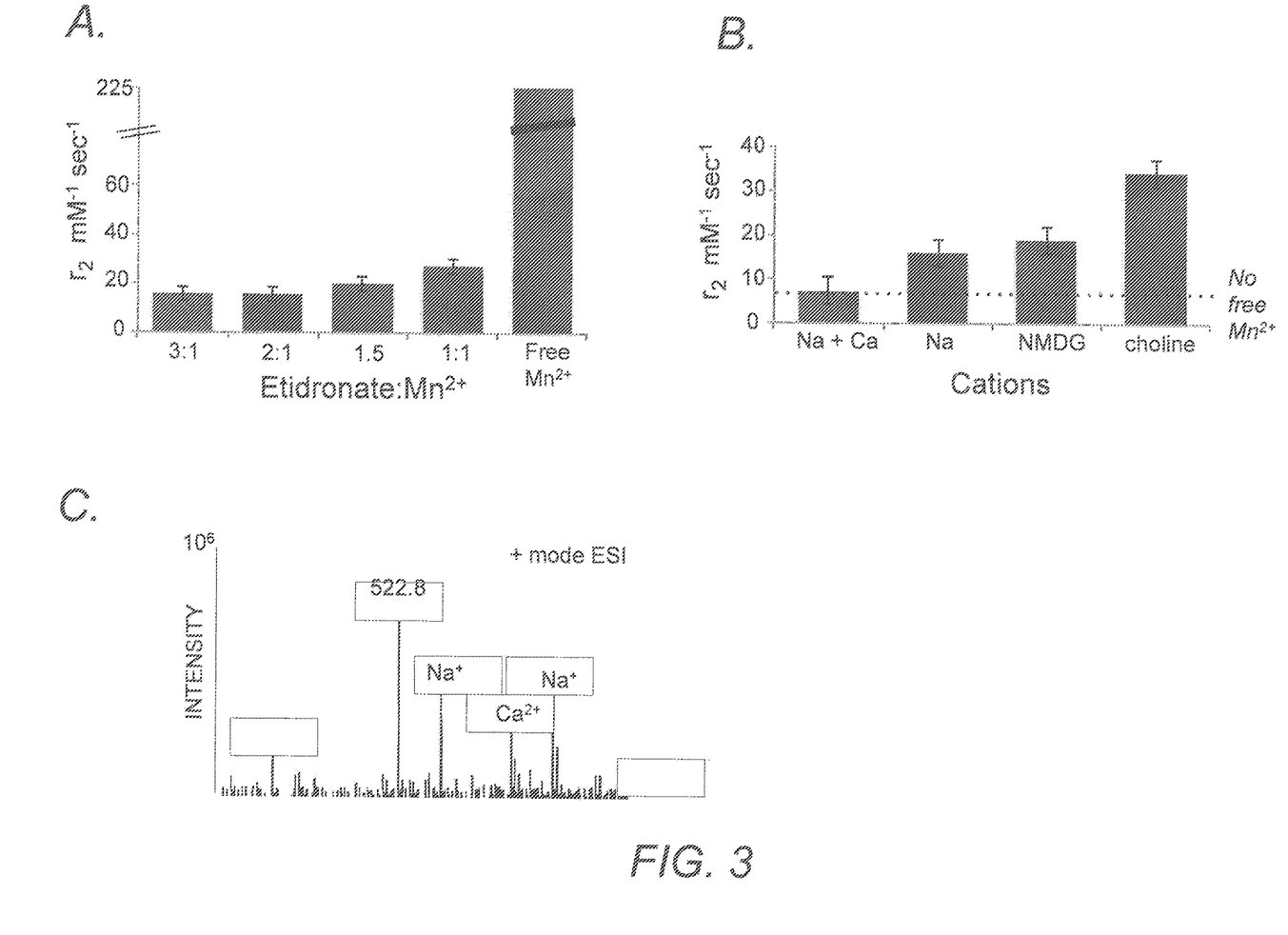

It was found that a 2:1 complex of 1-OH bisphosphonate and $Mn^{2+}$ is thermodynamically favored. By varying stoichiometry during synthesis, no additional complexation of $Mn^{2+}$ is observed when the ratio of bisphosphonate to $Mn^{2+}$ is raised above 2:1. (FIG. 3)

Free $Mn^{2+}$ is determined by measuring solvent $T_2$ as a function of time, since $r_2$ of $Mn^{2+}$ is 30-fold that of fully chelated, monohydrated $Mn^{2+}$ (Caravan et al., Mol. Imaging 2009, 4:89). Relaxivity measurements of 1-OH bisphosphonate:$Mn^{2+}$ complexes and $MnCl_2$ were performed at 7T at 22° C. in 2 mM Tris buffered $ddH_2O$. Sodium-containing solutions were titrated with NaOH to pH 7.0. Sodium-free solutions were titrated to neutral pH with the corresponding cation base (choline or meglumine). Stock solutions for each sample were prepared with 20 mM $Mn^{2+}$. $r_1$ and $r_2$ were calculated from conventional MR fast spin echo-based mapping methods for sample concentrations at 200 micromolar.

It was found that alkali metal cations increase the stability of the 2:1 bisphosphonate:$Mn^{2+}$ complex. Heteronuclear complexes containing at least one $Na^+$ cation and at least one $Ca^{2+}$ cation form the most stable 2:1 complexes, resulting in complete chelation of mono-hydrated $Mn^{2+}$ without excess ligand.

Example 3: Metal-Complexed 1-Hydroxy Ethane-1,1-Diphosphonic Acid-Derived Small Molecule Drugs for Modified Biodistribution, Diagnostic Imaging and Enhanced Therapeutic Activity

Mn bisphosphonate complexes afford new opportunities for creating an array of novel molecular imaging probes for MR imaging and image-guided therapy. 1-hydroxyethyl-enediphosphonates are readily amenable to coupling, either through their R2 group off the central carbon or by phosphate esterification, and can therefore be derivatized with many existing small molecule drugs that possess known targeting and/or therapeutic activities.

In addition to treatment of bone-related conditions, bisphosphonates have more recently shown significant promise as chemotherapeutic adjuncts for several malignancies. The mechanism of action is believed to be through inhibition of farnesyl disphosphate synthase (FDPS) and/or other intracellular enzymes that normally utilize pyrophosphate, the structural analogue of bisphosphonate. With the intracellular co-transport of bisphosphonates complexed with tumor-avid small molecules and Mn, bisphosphonates enable both molecular imaging and a second therapeutic activity in addition to that of the parent molecule.

Finally, it is worth noting that free Mn is believed to be toxic neurologically if allowed to accumulate to high concentrations in certain neuronal populations. When concentrations of Mn exceed the intracellular binding pool, Mn, as with Fe and other transition metals, fuels Fenton-mediated free radical production, particularly in the co-presence of elevated redox-active species such as $H_2O_2$, ascorbate, and quinones. Since Mn accumulation in tissues is readily visualized with MRI, however, selective delivery of Mn-containing agents is easily monitored. (Indeed, in whole animal MRI experiments with high-resolution quantitative $T_1$ mapping, no CNS accumulation of Mn was ever observed after administration of Mn bisphosphonate, even at >10× dose.) Selective accumulation of Mn in cancer cells, confirmed by MRI, thus may provide another means for therapy through redox-mediated cytotoxicity.

Figure 5:
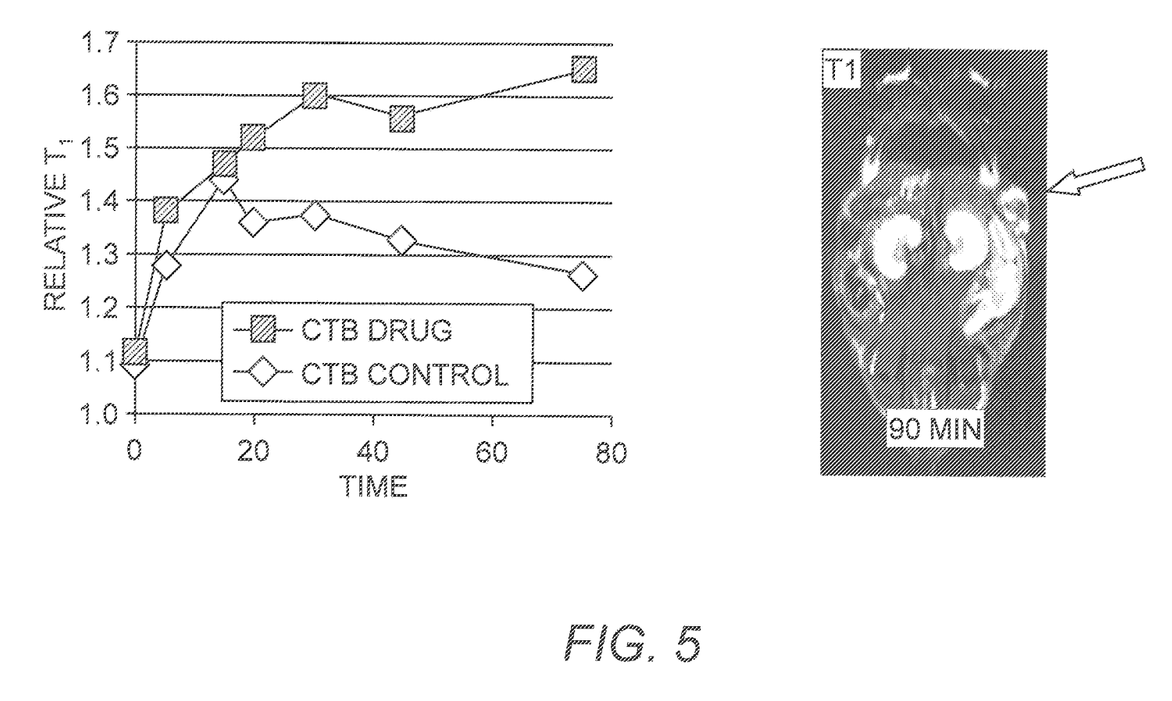
FIG. 5. Dynamic contrast enhancement of 4T1 tumor after i.v. administration of 1-hydroxybisphosphonate:Mn complex linked to HSP90 inhibitor as in Scheme 1C, 25 mg/kg. Graph on left depicts relative change in T1 enhancement in tumors after labeled drug (n=5) and after Mn:ETID complex alone (n=6).
Figure 6:
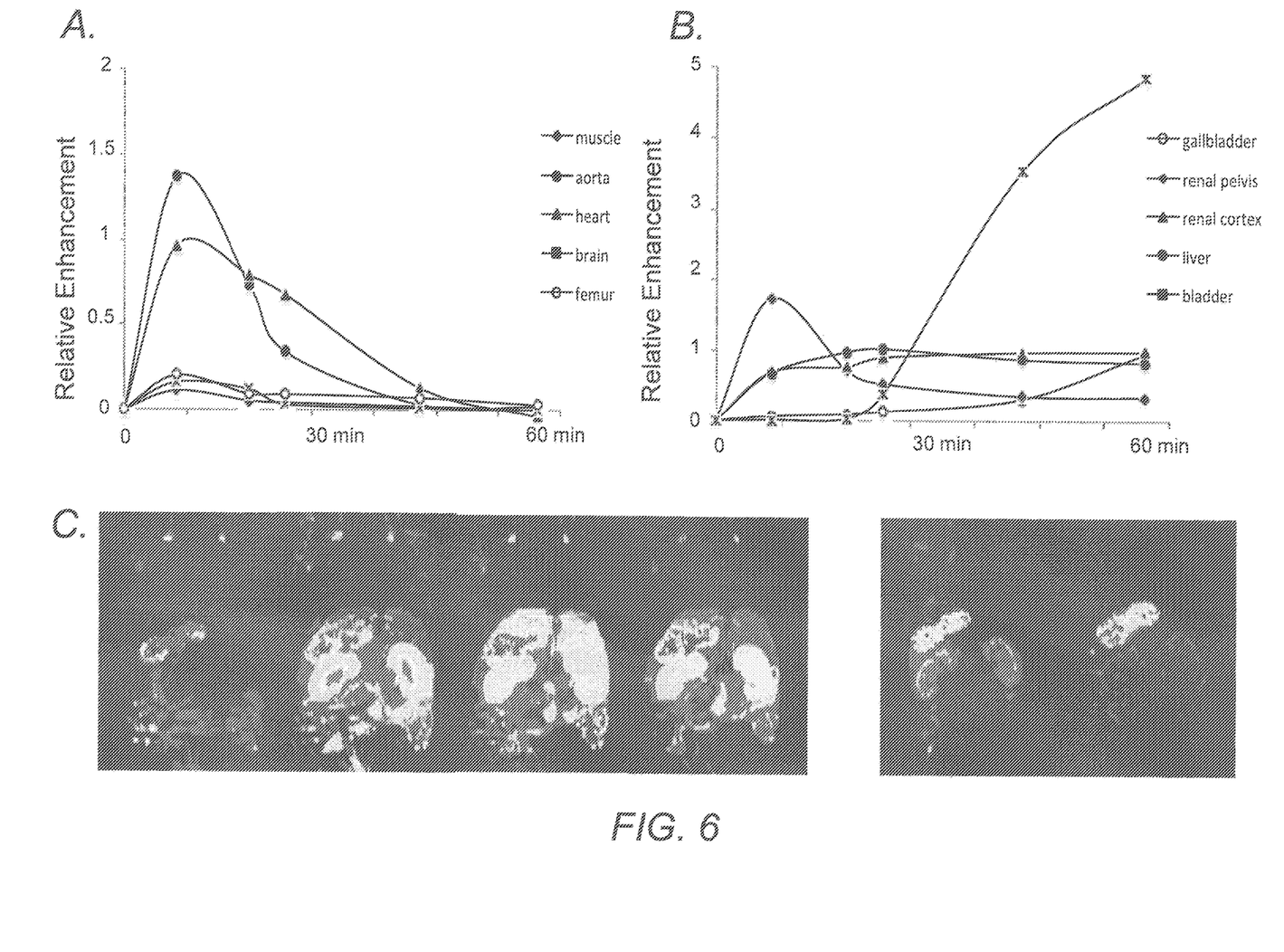

Several synthetic strategies were used for labeling small molecule drugs either directly or via polyethyleneglycol (PEG) linkers. Two complexes, the first with a medronate analogue (Scheme IB) via the amine-terminated PEG linker and the second an etidronate analogue coupled through the COOH-terminated PEG linker (Scheme 1C), were synthesized, characterized and studied preliminarily in vivo. Pilot data for both complexes show progressive accumulation of enhancement in 4T1 tumors that is greater than what is seen for the paramagnetic coordination complex alone (FIG. 5). Preliminary data on administration of the untethered HSP90i compound 30 min in advance of paramagnetic administration also suggest some competitive inhibition of paramagnetic (PM) complex from the parent drug.

Scheme 1. Bisphosphonate functionalized HSP90 inhibitors. A, Cancer cell-selective, 'high accumulating' HSP90 inhibitor is derivatized with a short PEG-linker, and linked to an amine group that does not interfere with the molecule's HSP90 selectivity. B, medronate analogue is then linked to the PEG. C, 1-hydroxybisphosphonate analogue is linked to the PEG.

Also synthesized was a 1-hydroxybisphosphonate derivative of the 4-aminoquinoline quinone reductase 2 inhibitor chloroquine, another well-characterized small molecule drug with high accumulative selectivity in many cancers. In addition to selective accumulation, chloroquine has shown recent promise as an effective adjunctive in chemotherapy trials.

Scheme 2. 1-hydroxybisphosphonate derivative of the 4-aminoquinoline chloroquine.

1-hydroxybisphosphonate functionalization of small molecule drugs may be accomplished through either direct conjugation of these molecules or through molecular bridges (e.g., PEG) linked to both these small molecules and 1-hydroxybisphosphonate analogues. They may be used to form subsequent metal complexes useful for diagnostic and/or therapeutic applications. Scheme 3 and Scheme 4 present example methods for direct linkages to an HSP90 inhibitor and to an FDA-approved drug lapatinib, a 'high-accumulating' tyrosine kinase inhibitor used for the treatment of some breast cancers.

Scheme 3. Commercially available 1-hydroxybiphosphonates with anime terminal R2 groups (above) and proposed synthesis for direct coupling of bisphosphonate to HSP90 inhibitor.

Scheme 4. Proposed synthesis for direct 1-hydroxybisphosphonate coupling of lapatinib.

-continued

R = H or C₂H₅

Example 4: Example Protocol for MRI-Guided Therapy

The introduction of paramagnetic functionality to therapeutic compounds enables real-time MR imaging of drug pharmacokinetics and biodistribution. In one example, a paramagnetic pharmaceutical is administered to a patient by a conventional route such as oral or intravenous delivery, and then an MRI scan is performed after administration to determine drug levels in various tissue compartments. MRI may be performed immediately following, within 1-24 hours, or within two or more days following drug administration, depending on the inherent biodistributive properties of a given pharmaceutical and the therapeutic goal. By utilizing quantitative (e.g., T1 mapping) and qualitative (e.g., T1 and T2-weighted) acquisition sequences for detection and measurement of drug accumulation in tissues, MRI is able to characterize the pharmacokinetic behavior of a given pharmaceutical in individual patients, thereby guiding optimal dosing so that therapeutic levels are achieved and accumulations minimized in healthy tissues.

In another example, a paramagnetic pharmaceutical is administered using a more direct route such as through an intravascular catheter (e.g., intra-arterial, intravenous) or percutaneously (e.g., needle placement, convection enhanced delivery), and MRI is performed in real-time in order to optimize precise local drug delivery to the target. In this particular application, MRI is used both to guide the in vivo placement of the delivery device (e.g., catheter or needle) and the administration of the pharmaceutical into its target.

In clinical practice, iodinated or Gadolinium-based contrast agents are currently used in analogous fashion, using x-ray/CT fluoroscopy or MRI guidance, respectively. These agents are employed under the assumption that they serve as surrogate markers of drug delivery, localization and distribution. This practice is common, for example, with the administration of anti-neoplastic drugs into tumors or tumor resection cavities. These contrast agents, however, are poor surrogates because they are unlinked to the therapeutic agents and invariably possess markedly distinct pharmaceutical properties (e.g., molecular weight, lipophilicity, charge).

For the inventions described herein, the MRI contrast signal becomes a precise marker for drug delivery, localization and distribution.

The foregoing is illustrative of the present invention, and is not to be construed as limiting thereof. The invention is defined by the following claims, with equivalents of the claims to be included therein.

That which is claimed is:

1. A compound useful as a magnetic resonance imaging (MRI) contrast agent and a therapeutic agent, said compound having a structure represented by:

Y—X—Z wherein,
X is Mn(II), and Y and Z are each independently a bisphosphonate of the formula:

wherein:
$R^1$ is —OH,
$R^2$, $R^3$, $R^4$, $R^5$ and $R^6$ are each independently H, alkyl, or -LR', wherein at least one of $R^2$, $R^3$, $R^4$, $R^5$ and $R^6$ is -LR',
wherein each L is present or absent and when present is a linking group, and
wherein each R' is independently a therapeutic agent, or a pharmaceutically acceptable hydrate thereof,
wherein said compound has a stoichiometry of 1:2 (Mn(II): bisphosphonate),
wherein said compound is a salt comprising at least one alkali metal and at least one alkaline earth metal, and
wherein the contrast agent has a molecular weight of less than 2,000 daltons.

2. The compound of claim 1, wherein $R^2$ is -LR', and $R^3$, $R^4$, $R^5$ and $R^6$ are each independently H or alkyl.

3. The compound of claim 1, wherein L comprises a poly(alkylene oxide).

4. The compound of claim 1, wherein said therapeutic agent is a cytotoxin.

5. The compound of claim 4, wherein said cytotoxin is an anti-cancer agent or an antimicrobial.

6. The compound of claim 4, wherein said cytotoxin is selected from the group consisting of: lapatinib, aminoquinolines, and HSP-90 inhibitors.

7. The compound of claim 1, wherein the contrast agent has a molecular weight of less than 800 daltons.

8. The compound of claim 1, wherein the compound is octahedral.

9. The compound of claim 1, wherein the compound is a monohydrate or a dihydrate.

10. The compound of claim 1, wherein the alkali metal comprises sodium or potassium.

11. The compound of claim 10, wherein the alkaline earth metal is selected from calcium and magnesium.

12. The compound of claim 1, comprising:
at least one water molecule coordinated with said Mn(II).

13. The compound of claim 1, wherein said compound has an $r_2$ relaxivity of 5 to 18 $mM^{-1}$ $sec^{-1}$ measured at 7 Tesla, 22 degrees Celsius, in 2 mM Tris buffered $ddH_2O$, pH 7.0.

14. The compound of claim 1, wherein said alkaline earth metal comprises calcium.

15. The compound of claim 14, wherein said alkali metal comprises sodium.

16. A composition comprising the compound of claim 1 in a pharmaceutically acceptable carrier.

17. The composition of claim 16, wherein said pharmaceutically acceptable carrier is water or phosphate buffered saline.

18. The composition of claim 16, wherein said composition has a pH of from 6.0 to 8.0.

19. A method of performing a magnetic resonance imaging (MRI) scan on a subject comprising:
performing the MRI scan; and
administering the compound of claim 1 to said subject prior to and/or during said performing the MRI scan.

20. A method of administering a therapeutic agent to a subject in need thereof, comprising administering the compound claim 1 to said subject in a treatment effective amount.

21. The method of claim 20, further comprising detecting the compound in said subject with MRI.

22. The method of claim 21, wherein said administering is adjusted based upon said detecting.

23. The method of claim 20, wherein said subject is in need of treatment for cancer.

24. The method of claim 20, wherein said subject is in need of treatment for a microbial infection.

25. The method of claim 24, wherein said microbial infection is a recalcitrant or chronic bacterial infection.

* * * * *